United States Patent [19]

Edwards

[11] 4,429,413
[45] Jan. 31, 1984

[54] FINGERPRINT SENSOR

[75] Inventor: David G. Edwards, Mount Laurel, N.J.

[73] Assignee: Siemens Corporation, Iselin, N.J.

[21] Appl. No.: 288,288

[22] Filed: Jul. 30, 1981

[51] Int. Cl.³ .............................................. G06K 9/28
[52] U.S. Cl. ..................................... 382/4; 324/71.1; 382/68
[58] Field of Search ................ 382/2, 4, 68; 324/71.1; 358/213

[56] References Cited

U.S. PATENT DOCUMENTS 3,622,989 11/1971 Dowdy.
3,781,855 12/1973 Killen ..................................... 382/4
3,993,888 11/1976 Fellman ................................. 382/4
4,053,228 10/1977 Schiller.
4,189,749 2/1980 Hiroshima et al. ................. 358/213
4,353,056 10/1982 Tsikos .................................... 382/4

OTHER PUBLICATIONS

Preliminary Date Sheet "Solid State Image Sensor Array RA100×100" to EG & G Reticon (3-10-80).
"Solid-State Imagers With Integrated Fixed-Pattern Noise Suppression" to Koch et al., Siemens Forsch.-u Entwickl.-Ber. Bd 8 (1979), Nr. 5.
"Vibrit-Piezokeramik von Siemens" Datenblatt-Stand Nov. 1980.

Primary Examiner—Leo H. Boudreau
Attorney, Agent, or Firm—Karl F. Milde, Jr.

[57] ABSTRACT

A fingerprint sensor for transforming the topological pattern of a finger into an electric output signal. The sensor includes an array of cells arranged beneath a contact surface for sensing the pressure and/or temperature variations existing at the surface as a result of a fingerprint pressed against it. Each cell includes a transistor set to operate at a point within its amplification range. This operating point is varied in dependence upon the pressure and/or temperature at the adjacent contact surface. A circuit is provided to measure the amount of current passing through the transistor in each cell and to derive an electrical output signal therefrom.

19 Claims, 10 Drawing Figures

FINGERPRINT SENSOR

BACKGROUND OF THE INVENTION

1. Field of the Invention

This invention relates in general to a device for identifying an individual by verification of his or her fingerprint. The invention relates in particular to a fingerprint sensor for transforming the information presented by the papillary structure of a finger into an electrical output signal.

2. Description of the Prior Art

Fingerprint identification systems which identify the crest-and-valley configuration of a finger pressed on a contact surface are well known in the art.

In various systems, the finger press is interrogated by a light beam directed through the front surface of a transparent finger bed. The interrogating beam is partially reflected at the back surface in accordance with the optical discontinuities created by the finger pressed on this surface. Thus, the reflected light contains finger press information which can be received by an optoelectric element. Such a sensor which is disclosed for example in U.S. Pat. No. 4,053,228 requires beam-scanning and focusing devices and is, therefore, relatively voluminous and complicated. Beam directing means are avoided, if the assembly is varied in the following manner: Radiation is passed through a plate-shaped finger bed by internal total reflection. The plate appears homogeneously dark for an array of photosensitive elements which extend in a plane parallel to the finger bed plate. Once the finger is pressed on the plate, the resilient plate surface is distorted and causes a light pattern corresponding to the impressed relief. This assembly which is described in the co-pending U.S. patent application Ser. No. 176,696 filed on Aug. 11, 1980 and assigned to the same assignee (now U.S. Pat. No. 4,340,300 issued July 20, 1982) can be implemented as a small sized unit composed of only a few parts. Yet, it has still the drawbacks common to all sensors operating with light: the need for using a power-consuming radiation source and optical elements such as filters or lenses to create an evaluable image of the finger relief.

Therefore, efforts have been made to replace light by another transducing medium. For instance, in U.S. Pat. No. 3,622,989 there is shown a fingerprint detection system in which a finger connected to a common bar is pressed against an array of sense electrodes and conductive contact is made between the contact bar and selected sense electrodes via the ridges of the finger surface. Using the finger's surface conductivity for generating a current distribution is theoretically a very promising approach. However, in practice it is difficult to achieve reproducible results. Virtually any impurity such as moisture or dust on the finger under interrogation or on the contact surface of the electrode array can adulterate the current distribution.

In the co-pending U.S. patent application Ser. No. 170,606, filed on July 21, 1980 and assigned to the same assignee (now U.S. Pat. No. 4,394,773 issued July 19, 1983), there is discussed a sensor for changing the pressure pattern of a fingerprint into a charge pattern by means of a piezoelectric substance. The charge pattern is subsequently measured by a charge-coupled device (CCD) matrix, for example, of the type disclosed in the *Preliminary Data Sheet for a Solid State Image Sensor Array RA* 100×100; EG & G Reticon, Sunnyvale, Calif.

SUMMARY OF THE INVENTION

1. Objects

It is, therefore, an object of the present invention to provide a fingerprint sensor for transforming the information contained in the epidermal structure of the finger into an electric output signal without an intermediate conversion into optical information.

Another object of the invention is to provide a fingerprint sensor which has small dimensions, is insensitive to mechanical influences and may easily be assembled from commercially available components.

Another object of the invention is to provide a fingerprint sensor that can be implemented in solid state technology with integrated circuits.

Still another object of the invention is to provide a fingerprint sensor which provides high sensibility and high reliability and requires minimum power.

These objects, as well as other objects which will become apparent from the discussion that follows are achieved, according to the present invention, by providing a contact body having a contact surface for receiving a finger under investigation; an array of sensing cells arranged adjacent the contact body and including a transistor in each cell; a circuit for measuring the amount of current passing through various transistors in the sensing cells; and a circuit for presetting the operating points of the transistors along their current (I) and voltage (V) characteristics in which they act as amplifiers. These operating points are affected, either directly or indirectly, by the topological pattern of a fingerprint.

According to the invention, therefore, the operating points of the transistors may be present prior to placing a finger on the contact surface and, when the contact pressure of the finger is thereafter exercised, the change in the operating points may be measured. Similarly, the operating points of the transistors may be preset while a contact pressure is exercised by a finger against the contact surface, and the change in operating points may be measured when the contact pressure is removed.

Essentially, the present invention is based on the principle that the operating point of a transistor amplifier may be varied by changing certain physical parameters to which it is subjected, such as ambient pressure, ambient temperature and ambient voltage. The topological pattern of a fingerprint, when pressed against a contact surface, results in corresponding variations in pressure and temperature at that contact surface. These variations in temperature and pressure may be sensed by the array of sensing cells, by directly changing the operating point of the transistor in each cell, or they may be sensed indirectly by a conversion into an electric voltage pattern. In particular, the pressure variations may be converted into a voltage pattern by a piezoelectric crystal, or the temperature variations may be converted into a voltage pattern by a pyroelectric crystal.

In a case where the array of sensing cells is directly responsive to either pressure or temperature, the operating points of the transistors may be varied by providing either a pressure or temperature-dependent resistor at each cell location in connection with the respective transistor at that location.

The read-out of the operating points of the transistors in the sensing cell array is preferably effected by a plurality of row conductors, each including a first and a second row line, and a plurality of column conductors. A row shift register having an input for receiving a row shift signal and a plurality of outputs is coupled to the row conductors; a column shift register having an input for receiving a column shift signal and a plurality of outputs is coupled to the column conductors. This arrangement permits interrogation of each of the sensing cells, in turn, to permit a read-out indicative of the topological pattern of the impressed finger.

For a full understanding of the present invention, reference should now be made to the following detailed description of the preferred embodiments of the invention and to the accompanying drawings.

DESCRIPTION OF THE PREFERRED EMBODIMENTS

Figure 1:
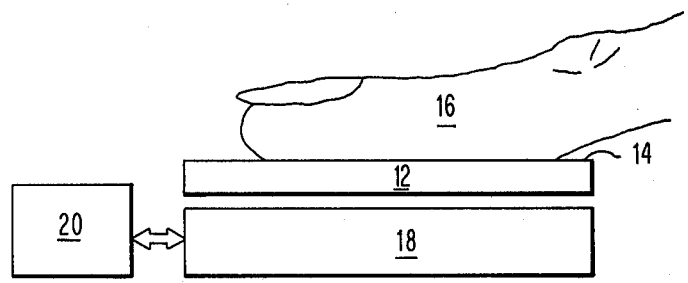
FIG. 1 is a side view of a fingerprint sensor of the type to which the present invention relates.

The preferred embodiments of the present invention will now be described with reference to FIGS. 1–10 of the drawings. Identical elements in the various figures are designated with the same reference numerals.

The basic requirements for a fingerprint sensor are to sense the ridge-shaped topological structure or "fingerprint" of the skin over an area of approximately 1.5 cm square with a resolution in the order of 0.1 mm. According to the invention, the topological structure is sensed by conversion of either the temperature or pressure at a fingerprint contact surface by monitoring the respective operating points of an array or matrix of transistors disposed adjacent to the contact surface. The operating points of these transistors are effected either directly or indirectly by the pressure and/or temperature pattern of the fingerprint. For direct measurement of pressure or temperature, the transistors may themselves have pressure or temperature dependent operating points or they may each be connected in a circuit comprising a resistor having a pressure or temperature dependent resistance value. For indirect measurement of pressure or temperature, the transistors may be influenced by variations in an electric charge originating from a piezoelectric or pyroelectric crystal layer. When pressure or temperature-sensitive resistors are employed, the operating points of the transistors will be dependent upon the instantaneous values of resistance which, in turn, depend upon the localized pressure or temperature. When a piezoelectric or pyroelectric crystal layer is employed, this layer converts a localized pressure or temperature, respectively, into a localized electric charge which, in turn, influences the operating points of the nearby transistors.

FIG. 1 shows a fingerprint sensor comprising a contact body 12 having a contact surface 14 for receiving a contact pressure exercised by a finger 16. The fingerprint at the ball of the finger forms a topological pattern which is converted into an information pattern formed by localized variations in the pressure and/or temperature on the contact surface. Immediately beneath the contact body is arranged an integrated circuit 18 forming an array of sensing cells, each in the order of 0.1 mm square. Each sensing cell includes a transistor having a gain, within an amplification range, that is dependent upon the most adjacent portion of the information pattern.

The integrated circuit 18 is connected to and driven by an electronic circuit 20 which includes means for presetting the operating points of the aforementioned transistors of the sensing cell array within their amplification ranges and means for measuring the amount of current passing through each transistor and deriving an electrical output signal therefrom.

Figure 2:
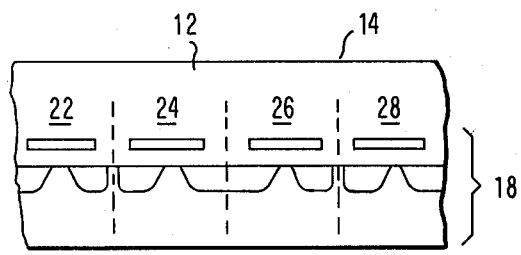
FIG. 2 is a cross-sectional diagram of a portion of the fingerprint sensor of FIG. 1.

FIG. 2 shows the structure of the device of FIG. 1 in greater detail. In particular, the integrated circuit 18 beneath the contact body 12 is provided with a number of field effect transistors 22, 24, 25 and 28 arranged in a regular matrix to form a plurality of sensing cells. The operating points of these transistors are affected, directly or indirectly, by the localized pressure and/or temperature applied by a finger to the contact surface 14.

Figure 3:
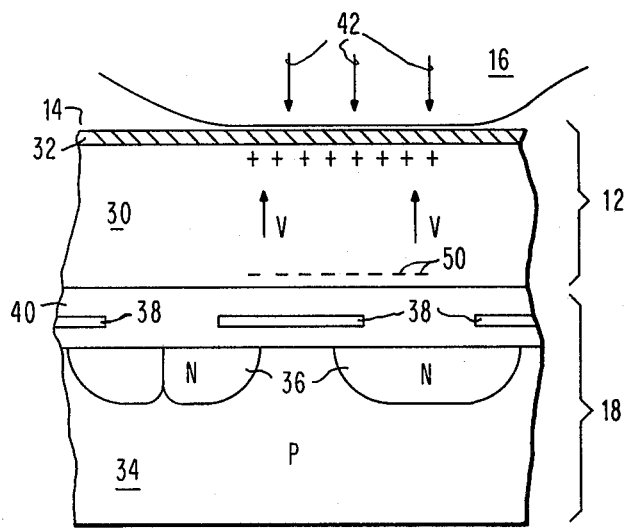
FIG. 3 is a cross-sectional diagram showing a detail of one preferred embodiment of the present invention.

The configuration and approximate sizes involved in a contact body and an adjacent integrated circuit are indicated in FIG. 3, which shows one preferred embodiment of the present invention. In this embodiment, the contact body comprises either a piezoelectric or pyroelectric crystal layer 30 sandwiched between a metallized layer 32 and the integrated circuit 18. The integrated circuit comprises a substrate 34 of P-type conductivity in which is diffused a multiplicity of regions 36 of N-type conductivity forming the source and drain electrodes of an array of N-channel field effect transistors. The conductivity types may, of course, be reversed to form P-channel transistors. Polysilicon gate electrodes 38 are disposed above the diffused N regions 36 and embedded in a layer 40 of insulating material. For example, if the substrate 34 is formed of silicon, the insulating layer 40 may be silicon dioxide ($SiO_2$). If necessary, the upper surface of the layer 40 may be ground flat to form an intimate contact with the planar surface of the crystal layer 30.

It may be possible to grow the crystal layer 30 directly on the surface of the insulating layer 40. Although this procedure simplifies fabrication, it may degrade the performance of the device since, for example, with a piezoelectric crystal the maximum piezoelectric effect is obtained from a monocrystalline structure of quartz ($SiO_2$), rather than the polycrystalline structure normally obtained in integrated circuit fabrication.

The metallized layer 32 on the crystal layer 30 is connected to ground potential so as to establish a well defined boundary condition for detection of the induced voltages. This layer forms the contact surface 14 for the finger 16.

When the finger 16 is pressed against the contact surface 14, localized charges are induced at the upper and lower surfaces of the crystal layer 30. The corresponding voltages across the crystal associated with these charges can easily be calculated. The pressure P of contact exerted by the finger 16 in the direction indicated by the arrows 42 is assumed to be 0.5 kg cm$^{-2}$. This pressure is obtained when a finger exerts a total force of 0.5 kg over an area of 2 cm$^2$, only half of which, because of the ridges, is in contact with the sensor. The induced voltage (V) in a piezoelectric crystal is given by $$V = \frac{dTh}{\epsilon\epsilon_o},$$

where
d=piezoelectric coefficient of the crystal material,
T=stress in the crystal=P×9.81,
h=thickness of the crystal, and
$\epsilon\epsilon_o$=permitivity of the crystal material.

The piezoelectric material may be quartz SiO$_2$ which is compatible with the fabrication of silicon integrated circuits. In this case, d=2.12×10$^{-12}$ coulombs/newton and $\epsilon\epsilon_o$=3.9, resulting in an induced voltage of 300 mv. This voltage is sufficient to effect the operating points of the field effect transistors arranged immediately below.

In the alternative, it is possible to utilize a much more sensitive piezoelectric ceramic material consisting of lead titanite, lead zirconate and lead nickel niobate (PbTiO$_3$, PbZrO$_3$ and PbNi$_\frac{1}{3}$Nb$_\frac{2}{3}$O$_3$). This material is commercially available from Siemens AG, Munich, West Germany, under the trademark VIBRIT®. Use of this material would result in an induced voltage of several volts.

For a temperature-sensitive device, the pyroelectric material may be commercially available polyvinylidenedifluoride (PVDF) which exhibits a charge pyrocoefficient of 2 nCb/cm$^2$ °C. and a voltage pyrocoefficient of 1100 V/cm °C.

Figure 4:
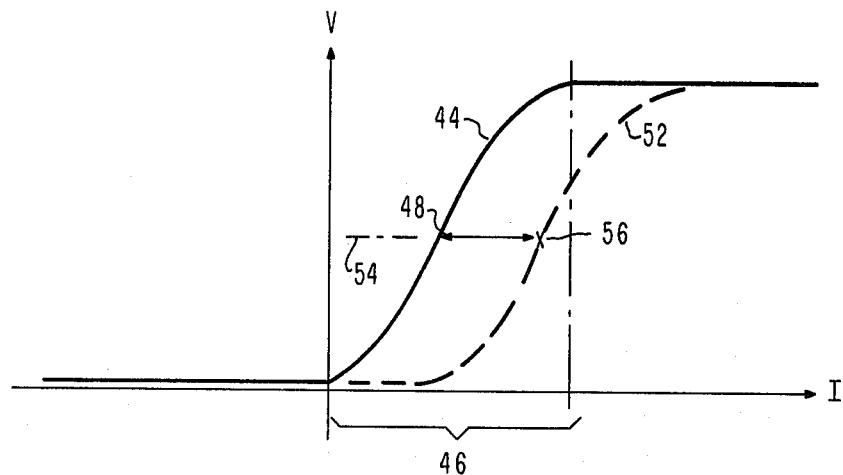
FIG. 4 is a current (I) vs. voltage (V) diagram of a transistor employed in the sensing array of the fingerprint sensor according to the present invention.

FIG. 4 shows a typical current (I)/voltage (V) characteristic 44 for a field effect transistor. The amplification range of the transistor having the characteristic 44 lies in the region 46. The operating point 48 is determined by the resistance in the source-drain path as well as by the voltage applied to the gate. If, however, an additional charge is present in the vicinity of the transistor gate, as indicated by the negative charges 50 in FIG. 3, the current-voltage characteristic of the transistor will be shifted as indicated by the dashed lines 52 in FIG. 4. As a consequence, the operating point will also be shifted along a constant voltage line 54 to a new point 56. The resultant shift in current flowing through the transistor may be monitored by a sensing circuit of the type illustrated in FIGS. 5–7 and described below.

Figure 5:
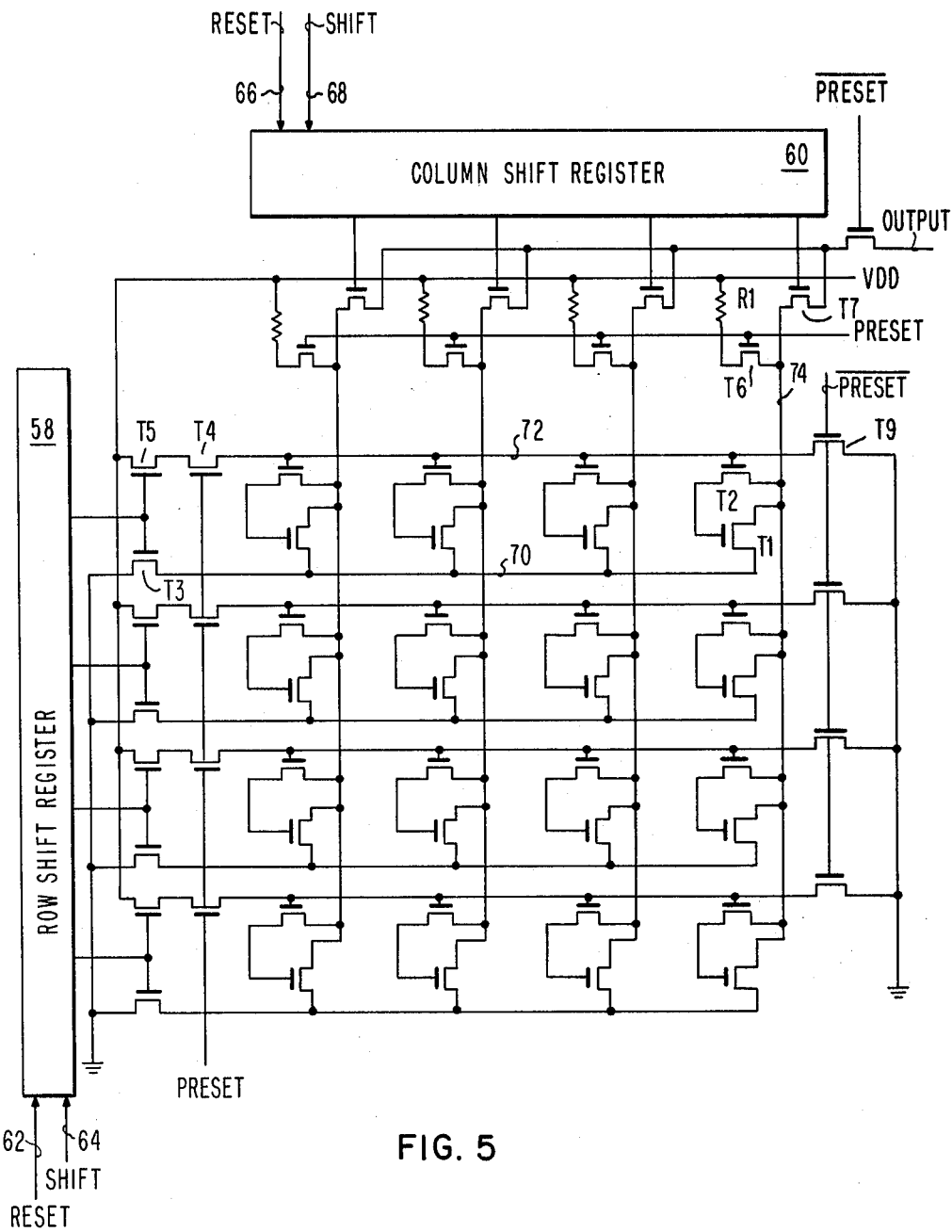
FIG. 5 is a schematic diagram of the sensing and read-out circuit according to one preferred embodiment of the present invention.

The sensing circuit is constructed in an array structure with between 100 and 200 elements on each side of the array, depending upon the required resolution. Such a sensing circuit is shown in FIG. 5 for the simplified case of a 4×4 array. The detailed circuit for one sense element is shown in FIG. 6.

Figure 6:
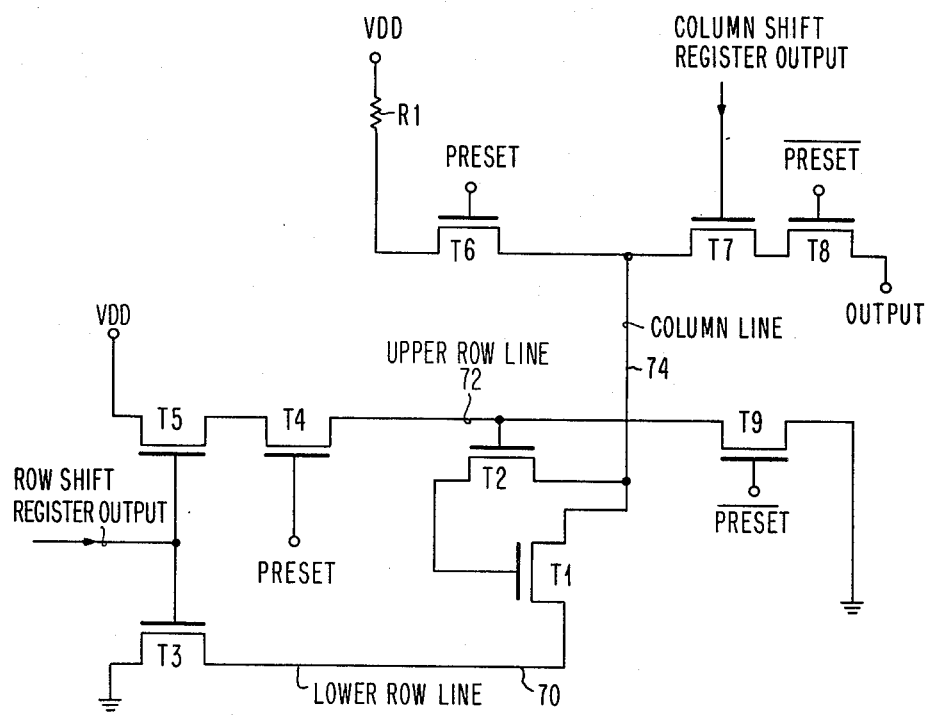
FIG. 6 is a schematic diagram of the read-out circuit for a single sense cell in the arrangement of FIG. 5.

The circuit of FIGS. 5 and 6 comprises a row shift register 58 and a column shift register 60. The row shift register is reset by a signal applied to a first input 62 and is incremented by a shift signal applied to a second input 64. Similarly, the column shift register is reset by a signal applied to a first input 66 and is incremented by a shift signal applied to a second input 68. The row and column shift registers each have four outputs (in the 4×4 array shown) which are successively activated as the respective register is shifted. The outputs of the row shift register are connected to the gates of transistors T3 and T5 (see FIG. 6) which connect a lower row line 70 and an upper line 72 to ground and to a supply voltage VDD, respectively. The outputs of the column shift register are each connected to the gate of a transistor T7 which connects a column line 74 with the circuit output. This column line is also connected via a transistor T6 and a resistor R1 to the supply voltage VDD. A sense transistor T1, constructed as shown in FIG. 3, and a control transistor T2 are arranged at the intersection of the two row lines 70 and 72 and the column line 74. The source and drain of the sense transistors connect the column line with the lower row line, whereas the source and drain of the control transistor T2 connects the column line 74 with the gate of the associated sense transistor T1. The gate of the control transistor T2 is connected to the upper row line which will either be at the supply voltage potential VDD, if the transistor T4 is conducting, or at ground potential if the transistor T9 is conducting.

Similarly, the column line 74 will either be connected to the supply voltage potential VDD via the resistor R1, if the transistor T6 is conducting, or to the circuit output if the transistor T8 is conducting. A signal PRESET is simultaneously applied to the transistors T4 and T6, while the inverted signal PRESET is applied to the transistors T8 and T9.

There are two methods of operating the sensing circuit of FIGS. 5 and 6. In one method the circuit is preset while the finger is pressed against the contact surface of the sensor, and then the information is read out after the pressure is removed. In the other method the circuit is preset in the absence of contact pressure by the finger, and then the information is read out while the finger is pressed against the contact surface. These two methods require the opposite polarity of piezoelectric or pyroelectric material. The first method, which is considered to be preferable because of the shorter time during which the finger must be stable on the sensor, comprises the following essential steps (assuming N-channel field effect transistors in the sensor array):

(1) A finger 16 is pressed against the contact surface 14 of a sensing element, triggering the ensuing steps (2) to (5);
(2) The column and row shift registers are reset;
(3) The signal PRESET goes high;
(4) The row shift register is activated, stepping through all of the rows. As each row is activated, its upper row line goes "high" and the lower row line is grounded. For each column, the transistor T2 conducts and connects the gate and drain of T1. The gate of T1 then settles to a voltage defined by the diode characteristic of T1 and the resistor R1. The value of R1 is chosen sufficiently high so that T1 will be just conducting;
(5) After thus presetting all the sense transistors, the PRESET signal goes low again;
(6) The finger 16 is removed from the contact surface 14, triggering the following step (7);
(7) The row and column shift signals are activated so as to step through the entire array, one cell of the matrix at a time. For each cell, the current which flows through the sense transistor T1 is measured and constitutes the sensor information output.

If P-channel field effect transistors are used, the polarity of the PRESET signal must be reversed so that transistors T4 and T6 are conducting, and transistors T8 and T9 are blocking when the PRESET signal is present.

The logic and control circuits illustrated in FIG. 5 as well as those circuits necessary to provide the drive signals PRESET, shift and reset for implementation of steps (1) to (7) above can be integrated into the semiconductor circuit together with the sensor cell array and along with the amplification circuits for the output signal. This integration is best carried out when the minimum configuration chip is already functioning.

Figure 7:
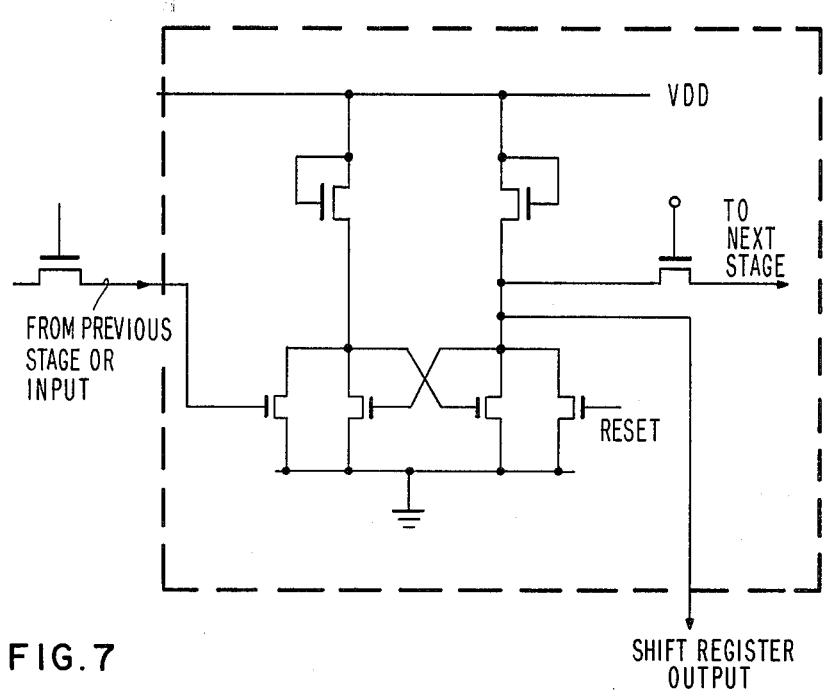
FIG. 7 is a schematic diagram of one stage of a shift register implemented with static flip flops.

The row and column shift registers 58 and 60 may be implemented either as dynamic shift registers or shift registers with static flip flops. For this application a shift register implemented with static flip flops, as illustrated in FIG. 7, is preferred. The large grid size of the sense cell matrix avoids any stringent requirements on the density of the layout. Decoders may also be used in place of the row and column shift registers, permitting random access to any point in the matrix. This random access could be of advantage if sophisticated software is used to produce enhanced pattern recognition. Of course, the decoders would require a multiplicity of address inputs, in place of the reset and clock inputs provided for the shift registers.

Figure 8:
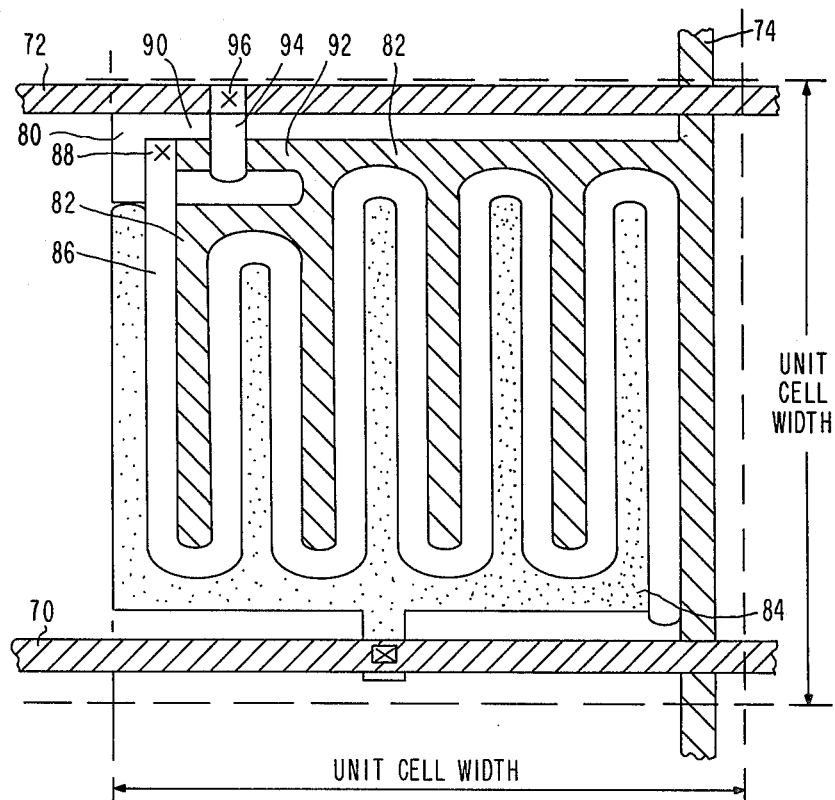
FIG. 8 is a topological layout of one cell of the sensing array, according to the present invention, which employs a piezoelectric or pyroelectric crystal.

A suitable layout for the sense cell is shown in FIG. 8. Most of the area of this cell is occupied by the large sense transistor T1. The remaining area of the cell is occupied by row and column lines and the small control transistor T2. This layout, which has a cell size of $200 \times 200$ $\mu$m (resulting in $100 \times 100$ elements in 2 cm$^2$) requires only a very conservative minimum dimension of 10 $\mu$m. Scaling to $150 \times 150$ $\mu$m ($130 \times 130$ elements in 2 cm$^2$) still only requires 7.5 $\mu$m minimum dimensions. As shown, the layout uses diffusion or implantation for the vertical column lines and polysilicon or metal for the horizontal row lines. These can be interchanged, if necessary, to minimize the capacitance of the row lines by using diffusion or implantation therefor.

More particularly, the layout of FIG. 8 includes a substrate 80 which supports the lower and upper row lines 70 and 72 of polysilicon or metal and a diffused or implanted column line 74. The diffused region extends from the vertical column line to a grid like structure 82 forming the drains for the transistors T1 and T2. A second diffused or implanted grid like area 84 is connected to the lower row line 70 and forms the source for the transistor T1. A serpentine layer of polysilicon 86 forming the gate of the transistor T1 is connected at point 88 to a diffused or implanted region 90 forming the source of the transistor T2. A section 92 of the diffused or implanted region 82 forms the drain for the transistor T2. A polysilicon or metal strip 94, connected at 96 to upper row line 72, forms the gate of the transistor T2.

In the sensing circuit described above, pressure or temperature variations on the contact layer 14 are used to indirectly influence the operating points of sensed transistors by conversion of these variations into the charge pattern using a piezoelectric or pyroelectric layer 30, respectively. Since variations in pressure and/or temperature change the conductivity of a transistor in a measurable manner, the same type of circuit may be employed as a sensing array in the fingerprint sensor without the intermediary of a piezoelectric or pyroelectric crystal layer. In the alternative, it is possible to employ a resistor which exhibits a strong dependency upon pressure and/or temperature in lieu of pressure/temperature dependent transistors. A suitable sensing circuit for use with a pressure and/or temperature-dependent resistor is shown in FIG. 9.

Figure 9:
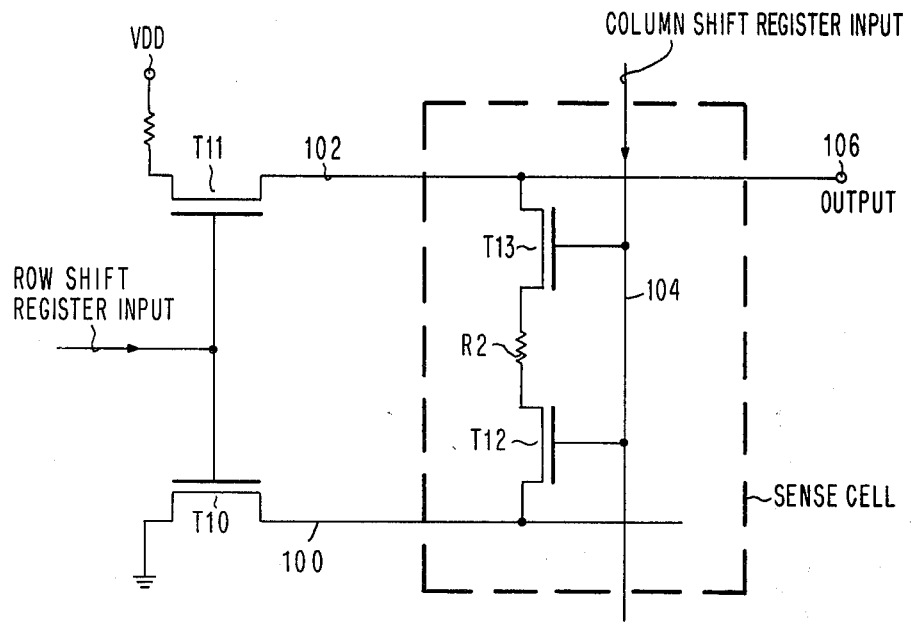
FIG. 9 is a schematic diagram of one sense cell employing a temperature or pressure-dependent resistor.

In FIG. 9, two row lines 100 and 102 are connected via transistors T10 and T11 to ground and to a voltage supply VDD, respectively. A column line 104 is connected to gates of two transistors T12 and T13 in a cell. When turned on by a singal on the column line, the cell transistors T12 and T13 interconnect the row and column lines 100 and 102 via a pressure and/or temperature dependent resistor R2. The current through the resistor R2 is reflected by the voltage on the output 106.

Figure 10:
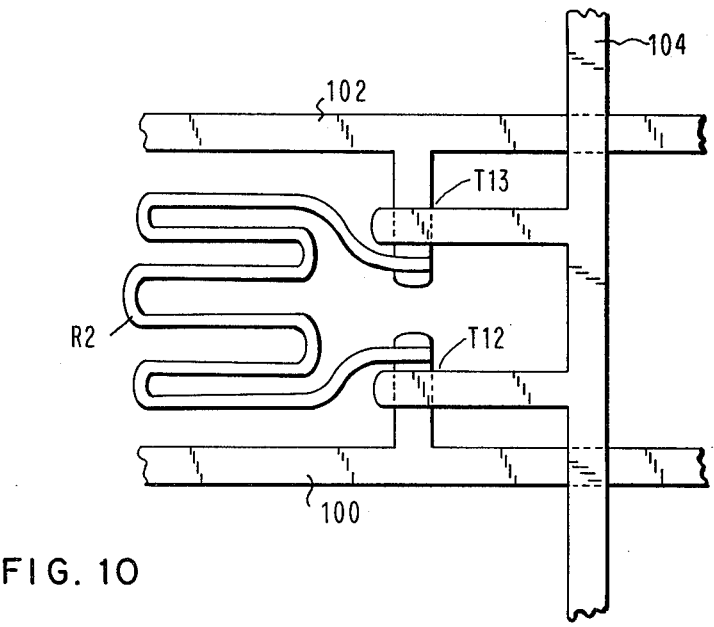
FIG. 10 is a topological layout of one cell of the sensing array shown in FIG. 9.

FIG. 10 shows the topological layout of the sense cell indicated in FIG. 9. The lower and upper row lines 100 and 102 are diffused or implanted regions, as are the sources and drains of the transistors T12 and T13. The column conductor 104 and the gates of the transistors T12 and T13 are polysilicon or metal. Finally, the pressure and/or temperature dependent resistor R2 is polysilicon.

The use of solid state sensors for fingerprint verification, according to the present invention, has a number of advantages over the optically based systems known in the prior art. Solid state sensors are compact, and, when produced in quantity, are cost effective, reliable and robust.

There has thus been shown and described a novel integrated circuit sensor for fingerprint verification which fulfills all the objects and advantages sought therefore. Many changes, modifications, variations and other uses and applications of the subject invention will, however, become apparent to those skilled in the art after considering this specification and the accompanying drawings which disclose preferred embodiments thereof. All such changes, modifications, variations and other uses and applications which do not depart from the spirit and scope of the invention are deemed to be covered by the invention which is limited only by the claims which follow.

What is claimed is:

1. A fingerprint sensor for transforming the topological pattern of a finger under investigation into an electric output signal, comprising
   (a) a contact body having a contact surface for receiving a contact pressure exercised by means of a finger and including a transducer element for transducing said topological pattern into a corresponding information pattern;
   (b) an array of sensing cells disposed adjacent said transducer element, each cell including a first transistor having a gain, within an amplification range, dependent upon the most adjacent portion of said information pattern;
   (c) means for setting the operating point of each of said first transistors within its amplification range; and
   (d) means for deriving said electrical output signal in dependence upon the current passing through said first transistors.

2. The fingerprint sensor of claim 1, wherein said, operating point setting means is actuated prior to exercising said contact pressure, and wherein said electrical output signal is responsive to the change in operating point when contact pressure is exercised.

3. The fingerprint sensor of claim 1, wherein said operating point setting means is actuated while said contact pressure is exercised and wherein said electrical output signal is responsive to the changer in operating point when said contact pressure is removed.

4. The fingerprint sensor of claim 1, wherein said information pattern is a pressure pattern.

5. The fingerprint sensor of claim 1, wherein said information pattern is a temperature pattern.

6. The fingerprint sensor of claim 1, wherein said information pattern is an electric voltage pattern.

7. The fingerprint sensor of claim 6, wherein said transducer element transduces said topological pattern into an intermediate pressure pattern and from said intermediate pressure pattern into said electrical voltage pattern.

8. The fingerprint sensor of claim 7, wherein said transducer element comprises a plurality of ohmic sense resistors, each having a pressure-dependent resistance and being connected to at least one of said transistors, for transducing said intermediate pressure pattern into said electric voltage pattern.

9. The fingerprint sensor of claim 7, wherein said transducer element comprises a piezoelectric layer for transducing said intermediate pressure pattern into said electric voltage pattern, said piezoelectric layer having a top surface adjacent said contact surface and a bottom surface adjacent said sensing cell array.

10. The fingerprint sensor of claim 6, wherein said transducer element transduces said topological pattern into an intermediate temperature pattern and from said intermediate temperature pattern into said electric voltage pattern.

11. The fingerprint sensor of claim 10, wherein said transducer element comprises a plurality of ohmic sense resistors, each having a temperature-dependent resistance, and being connected to at least one of said transistors, for transducing said intermediate temperature pattern into said electric voltage pattern.

12. The fingerprint sensor of claim 10, wherein said transducer element comprises a pyroelectric layer for transducing said intermediate temperature pattern into said electric voltage pattern, said pyroelectric layer having a top surface adjacent said contact surface and a bottom surface adjacent said sensing cell array.

13. The fingerprint sensor of claim 1, wherein said sense cell array includes a plurality of row conductors, each comprising a first and a second row line, and a plurality of cloumn conductors, wherein each sense cell includes a second transistor in addition to said first transistor, the source and the drain of said first transistor connecting one of said column conductors with said first row line of one of said row conductors and the source and the drain of said second transistor connecting said column conductor with the gate of said first transistor, the gate of said second transistor being connected with said second row line of said row conductor, wherein said first row line is connected to ground via a first row conductor switch, wherein said second row line is connected to a first voltage source via a second row conductor switch and wherein said column conductor is connected to a second voltage source via a first column conductor switch and to a terminal via a second column conductor switch, said terminal supplying said electric output signal.

14. The fingerprint sensor of claim 13, wherein said first and second row conductor switches and said first and second column conductor switches are switching transistors.

15. The fingerprint sensor of claim 13, further comprising a row shift register with an input for receiving a row shift signal and a plurality of outputs each of which control said first and second row conductor switches of one of said row conductors and a column shift register with an input for receiving a column shift signal and a plurality of outputs each of which control one of said column conductor switches.

16. The fingerprint sensor of claim 15, wherein said shift registers are implemented as dynamic shift registers.

17. The fingerprint sensor of claim 15, wherein the shift registers are implemented with static flip-flops.

18. The fingerprint sensor of claim 15, wherein said operating point setting means include preset row conductor switches and preset column conductor switches, each of said preset row conductor switches being inserted in one of said second row lines between the gates of said second transistor and said second row conductor switch, and each of said preset column conductor switches being connected between one of said column conductors and said second voltage source.

19. The fingerprint sensor of claim 13, wherein the potentials of said first and second voltage sources are identical.

* * * * *